Figure 2:
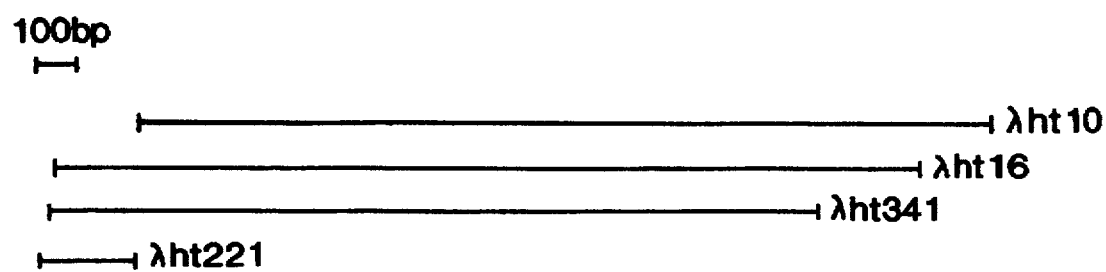

United States Patent [19]

Soubrier et al.

[11] Patent Number: 5,801,040

[45] Date of Patent: Sep. 1, 1998

[54] NUCLEIC ACID CODING FOR THE HUMAN TESTICULAR ANGIOTENSIN CONVERTING ENZYME (ACE) AND ITS USES, ESPECIALLY FOR THE IN VITRO SCREENING FOR THIS ENZYME IN THE ORGANISM

[75] Inventors: Florent Soubrier; François Alhenc-Gelas, both of Paris; Christine Hubert, Sevres, all of France

[73] Assignee: Institut National de la Sante et de la Recherche Medicale, Paris, France

[21] Appl. No.: 481,626

[22] Filed: Jun. 7, 1995

Related U.S. Application Data

[63] Continuation of Ser. No. 272,283, Jul. 8, 1994, abandoned, which is a continuation of Ser. No. 656,183, filed as PCT/FR90/00513, Jul. 5, 1990 published as WO91/00354, Jan. 10, 1991, abandoned.

[30] Foreign Application Priority Data

Jul. 5, 1989 [FR] France ............... 8909062

[51] Int. Cl.$^6$ ............... C12N 15/57; C12N 9/64
[52] U.S. Cl. ............... 435/226; 435/69.1; 435/69.8; 435/6; 435/7.4; 435/172.3; 435/320.1; 435/325; 435/252.3; 530/324; 530/325; 530/326; 530/327; 530/328; 530/329; 530/330; 530/387.9; 536/23.1; 536/23.2; 536/24.3; 536/24.31; 536/24.33; 935/14; 935/27; 935/56; 935/78
[58] Field of Search ............... 435/226, 69.8, 435/69.1, 7.4, 6, 172.3, 320.1, 240.2, 252.3; 530/324, 325, 326, 327, 328, 329, 330, 387.9; 536/23.1, 23.2, 24.3, 24.31, 24.33; 935/14, 27, 56, 71, 78

[56] References Cited

U.S. PATENT DOCUMENTS 4,276,378   6/1981   Ryan et al. ............... 435/23

4,965,188  10/1990   Mullis et al. ............... 435/6

OTHER PUBLICATIONS

J.S. Powell et al. "Human Erythropoietin Gene; High Level Expression In Stably Transfected Mammalian Cells and Chromosome Localization", Proc. Natl. Acad. Sci. 83: 6465–6469, Sep. 1986.

Soffer, et al.; Clin. Experimental Hypertension, 9(2–3) 229–234 (1987).

Lattion, et al.; FEBS Lett. 252 (1,2):99–104 (1989).

Ehlers, et al.; PNAS (USA) 86(20):7741–45 (1989).

Soubrier, et al.; PNAS (USA) 85:9386–90 (1988).

Lanzillo, et al.; Biochem Biophys Res. Com. 128(1):457–463 (1985).

Yasui, et al.; Chem. Abstr. 101(25):506, 227493r (1984).

Roy, et al.; Biochem Biophys Res. Com. 155(2):678–684 (1988).

Berger, et al.; eds., Methods in Enz., vol. 152, pp. 393–399, 415–423, 423–447, 661–704 (1987).

*Primary Examiner*—Rebecca E. Prouty
*Attorney, Agent, or Firm*—Finnegan, Henderson, Farabow, Garrett & Dunner

[57] ABSTRACT

The object of the invention is the cloning and sequencing of the nucleic acid coding for the human testicular ACE as well as the determination of the peptide sequence of this ACE.

It relates more particularly to the use of nucleotide probes capable of hybridizing with all or part of the above-mentioned nucleic acid, and also the polyclonal or monoclonal antibodies recognizing specifically all or part of the above-mentioned peptide sequence, and the use of these probes or these antibodies for the implementation, respectively, of a method for the detection of the messenger RNA coding for the testicular ACE in vitro or of the testicular ACE directly.

13 Claims, 4 Drawing Sheets

```
AGCTGCAGGACTCTGCTCTCCTGCGGCCAGGGTTGGGCTACTGCAGGACTTCCCAGCCTC
                         MetGlyGlnGlyTrpAlaThrAlaGlyLeuProSerLeu
                           1                              10

CTCTTCCTGCTCTGCTACGGGCACCCTCTGCTGGTCCCTAGCCAGGAGGCATCCCAACAGGTG 133
LeuPheLeuLeuCysTyrGlyHisProLeuLeuValProSerGlnGluAlaSerGlnGlnVal
                    20                              30

ACAGTCACCCATGGGACAAGCAGCCAGGCAACAACCAGAACAACCACCACCACCAGGCGACGGCC
ThrValThrHisGlyThrSerSerGlnAlaThrThrThrThrHisGlnAlaThrAla
           40                              50

CACCAGACATCAGCCCAGAGCCCAAACCTGGTGACTGATGAGGCTGAGGCCAAGTTTGTGGAG 268
HisGlnThrSerAlaGlnSerProAsnLeuValThrAspGluAlaGluAlaSerLysPheValGlu
             60                              70                  80

GAATATGACCGGACATCCCAGGTGGTGTGGAACGAGTATGCCGAGGCCAACTGGAACTACAACCAAC
GluTyrAspArgThrSerGlnValValTrpAsnGluTyrAlaGluAlaAsnTrpAsnTyrAsnThrAsn
                 90                              100

ATCACCAGAGACCAAGATTTCTGCTGCAGAAGAACATGCAAATAGCCAACACCCCTGAAG 403
IleThrThrGluThrSerLysIleLeuLeuGlnLysAsnMetGlnIleAlaAsnHisThrLeuLys
              110                              120

TACGGCACCCAGGCCAGGAAGTTTGATGTGAACCAGTTGCAGAACACCACTATCAAGCGGATCATAAAG
TyrGlyThrGlnAlaArgLysPheAspValAsnGlnLeuGlnAsnThrThrIleLysArgIleIleLys
                130                              140

AAGGTTCAGGACCTAGAGACCCAGGCCAGGGGCTGCCTGCCCCAGGAGCTGGAGGAGTACAACAAGATCCTG 538
LysValGlnAspLeuGluThrGlnAlaArgGlySerLeuProGlnGluLeuGluGluTyrAsnLysIleLeu
             150                              160                   170

TTGGATATGATGGAAACCACTACAGGCTGGCCACTGTGTGCCAGCTGTGCCAGCTGCCTGCAGCTCGAG
LeuAspMetMetGluThrThrThrTyrSerValAlaThrValCysHisProAsnGlySerCysLeuGlnLeuGlu

CCAGATCTGACGAATGTGATGGCCACCATCCCGGAAATATGAAGACCTGTTATGGGCATGGGAGGGC 673
ProAspLeuThrAsnValMetAlaThrIleProGluLysTyrGluAspLeuLeuTrpAlaTrpGluGly
                200                              210

TGGCGAGACAAGGCGGGAGAGCCATCCTCCAGTTTACCCGAAATACGTGGAACTCATCAACCAGGCT
TrpArgAspLysAlaGlyArgAlaIleLeuGlnPheTyrProLysTyrValGluLeuIleAsnGlnAla
               220                              230
```

FIG. 1A

```
GCCCGGCTCAATGGCTATGTAGATGCAGGGGACTCGTGGAGGTCTATGTACGAGACACCATCCCTG  808
AlaArgLeuAsnGlyTyrValAspAlaGlyAspSerTrpArgSerMetTyrGluThrProSerLeu
         240                    250                    260
GAGCAAGACCTGGAGCGGCTCTTCCAGGAGCTGCAGCCACTCTACCTGCCATGCCTACGTGCGC
GluGlnAspLeuGluArgLeuPheGlnGluLeuGlnProLeuTyrLeuAsnLeuHisAlaTyrValArg
                270                    280
CGGGCCCTGCACCGTCACTACGGGGCCCAGCACATCAACCTGGAGGGGCCCATTCCTGCTCACCTG  943
ArgAlaLeuHisArgHisTyrGlyAlaGlnHisIleAsnLeuGluGlyProIleProAlaHisLeu
                        290                    300
CTGGGGAACATGTGGGCGGCAGACCTGGTCCAACATCTATGACTTGGTGGTGCCCTTCAGCCCCC
LeuGlyAsnMetTrpAlaGlnThrTrpSerAsnIleTyrAspLeuValValProPheProSerAlaPro
            310                    320
TCGATGGACACCACAGAGGCTATGCTAAAGCAGGGCTGGAACGCCAGGAGGATGTTAAGGAGGCT  1078
SerMetAspThrThrGluAlaMetLeuLysGlnGlyTrpThrProArgArgMetPheLysGluAla
                330                    350
GATGATTTCTTCACCTCCCTGGGCCCGTGCTCCTGAGTTCTGGAACAAGTCGATGCTGGAG
AspAspPhePheThrSerLeuGlyLeuLeuProValProProGluPheTrpAsnLysSerMetLeuGlu
        340                    360                    370
AAGCCAACCGACGGGGAGGTGGTCTGCCACGTCGCCAGCACCTTCTACAACGGCAAGGAC  1213
LysProThrAspGlyArgGluValValCysHisAlaSerAlaTrpAspPheTyrAsnGlyLysAsp
                380                    390
TTCCGGATCAAGCAGTGCACCACCGTGAACTTGGAGGACCTGGTGGCCCACCACGAAATGGGCCAC
PheArgIleLysGlnCysThrThrValAsnLeuGluAspLeuValAlaHisHisGluMetGlyHis
        400                    410
ATCCAGTATTTCATGCAGTACAAGACTTACCTGTGGCCTTGAGGGAGGGTGCCAACCCCGGCTTC  1348
IleGlnTyrPheMetGlnTyrLysThrTyrLeuTrpProValAlaLeuArgGluGluValAlaAsnProGlyPhe
            420                    430                    440
CATGAGGGCCATTGGGACGTGCTAGCCCTCAGTGTCTCAGCCCAAGACCACCAGTCTCAACCTG
HisGluGlyHisTrpAspValLeuAlaLeuSerValSerThrProLysHisLeuHisSerLeuAsnLeu
                    450                    460
CTGAGCAGTGAGGGTGGCAGCGACGATGACATCAACTTTCTGATGAAGATGGCCCTTGACAAG  1483
LeuSerSerGluGlyGlySerAspAspAspIleAsnPheLeuMetLysMetAlaLeuAspLys
                            470                    480
```

FIG. 1B

FIG. 1C

```
ATGGCCTTTATCCCCTTCAGCTACTACCTCGTCGATCAGTGGGCGCTGGAGGGTATTTGATGGAAGCATCACC
IleAlaPheIleProPheSerTyrTyrLeuValAspGlnTrpArgTrpLeuGluGlyTyrLeuMetGluHisHis
                                490
AAGGAGAACTATAACCAGGAGTGGTGGAGCTTCAGGCTGAAGTACCAGGGCCTTGCCCCCAGTG  1618
LysGluAsnTyrAsnGlnGluTrpTrpSerPheArgLeuLysTyrGlnGlyLeuCysProProVal
        510                                          520              530
CCCAGGACTCAAGGTGACTTTGACCCAGGGCCAAGTTCCACATTCCTTCTAGCGTGCCTTACATCAGG
ProArgThrGlnGlyAspPheAspProGlyAlaLysPheHisIleProSerValProTyrIleArg
                                540                              550
TACTTTGTCAGCTTCATCATCCAGTTCCAGTTCCACGAGGCACTGTGCCAGGCAGCTGGCCACACG  1753
TyrPheValSerPheIleIleGlnPheGlnPheHisGluAlaLeuCysGlnAlaAlaGlyHisThr
                                560                              570
GGCCCCCTGCACAAGTGTGACATCTACCAGTTCCAAGGAGGCCGGGCAGCGTGGGCAGCGCCATGAAG
GlyProLeuHisLysCysAspIleTyrGlnPheGlnSerLysGluAlaGlyAlaArgLeuAlaThrAlaMetLys
                                580                              590
CTGGGCTTCAGTAGGCCGTGGCCGAAGCCATGCAGCTGATCACGGGCCAGCCAACATGAGGCGC  1888
LeuGlyPheSerArgProTrpProGluAlaMetGlnLeuIleThrGlyGlnProAsnMetSerAla
        600                                          610              620
TCGGCCATGTTGAGCTACTTCAAGCCGCTGCTGCTGCCACCGGAGAACGAGTGTGATGGGAGAG
SerAlaMetLeuSerTyrPheLysProLeuLeuLeuProAsnGluThrGluAsnGluLeuHisGlyGlu
                                630                              640
AAGCTGGGCTGGCCGCAGTACAACTGGACGCCGAACTCCGCTCAGAAGGGCCCCTCCCAGAC  2023
LysLeuGlyLeuTrpProGlnTyrAsnTrpThrProAsnSerAlaArgSerGluGlyProLeuProAsp
                                650                              660
AGCGGCCGCGTCAGCTTCCTGGACCTGGATGCGCAGCAGGCCCCGCGTGGGCAGTGGCTGCTG
SerGlyArgValSerPheLeuAspLeuAspLeuAlaGlnAlaGlnGlnAlaArgValGlyGlnTrpLeuLeu
                                670                              680
CTCTTCCTGGGCATCGCCCTGTGCTAGCACCAGCCCCTGGGCCTCAGCCAGGGCCTCTTCAGCATCCGC  2158
LeuPheLeuGlyIleAlaLeuLeuValAlaThrLeuGlyLeuSerGlnArgGlyPheSerIleArg
        690                                          700              710
CACCGCAGCCTCCACCGGCACTCCCAGGGCCCCAAGGGCCTCCAGGTGGAGTGAGACACTCCTGA
HisArgSerLeuHisSerHisSerHisGlyProGlnPheGlySerGluValGlyLeuArgHisSer*
                                720                              730
GGTGACCCGGCTCGGGCTGGGTCGGAGACACCCCACCAGCCCCTGCCCAAGGGGCCTCCACCCTGCCGATGGAACACTGGTG  2293

GGCAGCTGAGGACACACCCCACCAGCCGCCCCACACCCAGCCCAGCCCCTTCTCCCAGCACACGGCTGCTGACACTGAGCC  2428

TCCCAGTCCTCCACCAGTCTCCCTGTGAATACAATTAAAGGTCCTGCCCTCCCC

CCACCCTCTCCAAGTCTCCCTGTGAATACAATTAAAGGTCCTGCCCTCCC(A)  2477
```

NUCLEIC ACID CODING FOR THE HUMAN TESTICULAR ANGIOTENSIN CONVERTING ENZYME (ACE) AND ITS USES, ESPECIALLY FOR THE IN VITRO SCREENING FOR THIS ENZYME IN THE ORGANISM

This is a continuation of application Ser. No. 08/272,283, filed Jul. 8, 1994, which is a continuation of application Ser. No. 07/656,183, filed as PCT/FR90/00513, Jul. 5, 1990 published as WO91/00354, Jan. 10, 1991, both now abandoned.

The invention relates to a nucleic acid coding for the angiotensin converting enzyme (ACE) in the germinal cells of human testicles as well as to vectors containing this nucleic acid and the utilization of these latter for the production of this enzyme. The invention also relates to the uses of this nucleic acid, especially for the in vitro screening for this enzyme in the organism.

The ACE, or peptidyl dipeptidase A (EC 3.4.15.1), or also kininase II, plays an important role in the regulation of arterial blood pressure by hydrolysing angiotensin I (inactive peptide released by cleavage of angiotensinogen by renin) to angiotensin II, a vasopressor agent playing a major role in the regulation of arterial blood pressure (SKEGGS, L. T. et al (1956) *J. Exp. Med.*, 103, 295–229).

The inhibition of the activity of the ACE by EDTA and metal chelators indicates that it is a metallopeptidase, more particularly a zinc peptidase capable of hydrolysing not only angiotensin I but also bradykinin (a vasodilating and natriuretic peptide which it converts into an inactive heptapeptide), and many other peptides with biological activity (YANG, H. Y. T. et al (1970) Biochim. *Biophys. Acta* 214, 374–376; ERDOS, E. G. et al (1987), *Lab. Invest.*, 56.

The ACE is a peptidase widely distributed in the organism which is found, for example, in the form of a membrane enzyme at the surface of the vascular endothelial cells and renal epithelial cells, as well as in the form of an enzyme circulating in the plasma (ERDOS et al (1987) cited above; CARDWELL, P. R. B. et al, (1976), *Science* 191, 1050–1051; RYAN, U. S. et al (1976) *Tissue Cell*, 8, 125–145).

Methods for the purification of human or animal endothelial ACE have already been described (in particular in BULL H. G. et al, (1985) *J. Biol. Chem.*, 260, 2963–2972; HOOPER, N. M. et al, (1987) *Biochem. J.*, 247, 85–93), and some peptide sequences of the endothelial ACE of animal origin have been published (BERNSTEIN, K. E. et al (1988), *Kidney Int.*, 33, 652–655; HARRIS, R. B. et al (1985) *J. Biol. Chem.*, 260, 2208–2211; IWATA, K. et al (1982), *Biochem. Biophys. Res. Commun.*, 107, 1097–1103; IWATA, K. et al (1983) *Arch. Biochem. Biophys.*, 227, 188–201; ST CLAIR, D. K. et al (1986), *Biochem. Biophys. Res. Commun.*, 141, 968–972; SOFFER, R. L. et al (1987) *Clin. Exp. Hyp.* A9, 229–234).

Some attempts to clone the DNA coding for the animal ACE have been carried out starting from two organs rich in ACE, the kidneys and the lungs, but no complete nucleic acid sequence coding for the animal ACE has, however, been described; several fragments only of such a nucleic acid have been described (DELUCA-FLAHERTY, C. et al (1987), *Int. J. Peptide Protein Res.*, 29, 678–684; BERNSTEIN, K. E. et al. (1988), *J. Biol. Chem.*, 263, 11021–11024). The quantities of messenger RNA (mRNA) coding for the ACE are probably too small in these organs for the cloning of a complementary DNA (cDNA) of this mRNA to be easily performed.

The cloning of the DNA coding for the ACE of human endothelial cells was carried out for the first time by the authors of the present application; the complete nucleotide sequence of the DNA coding for the endothelial ACE as well as the amino acid sequence of this latter are described in the article by SOUBRIER F. et al published in *Proc. Natl. Acad. Sci.*, USA, 85, pp 9386–9390 (1988).

An enzymatic activity of the ACE type has also been demonstrated in human and animal testicles (J. J. LANZILLO et al., *J. Biol. Chem.*, 260, pp 14938–14944 (1985)).

However, the structure of the ACE of human testicles (or also designated by the expression testicular ACE) is not known at present; and no sequence of the DNA coding for this testicular ACE has been described hitherto. S. N. ROY et al. claim, in an article in *Biochem. Biophys. Res. Commun.* 155: 678–684 (1988), to have isolated clones but they do not give the sequence of the clones.

The specific object of the present invention is the cloning and sequencing of the nucleic acid coding for human testicular ACE; this work was carried out starting from two libraries of DNA complementary to mRNA derived from human testicles and nucleotide probes corresponding to the endothelial ACE. The techniques used for the cloning and sequencing of the nucleic acid according to the invention will be more particularly described in the detailed description of the invention.

Reference will be made in what follows to the figures in which:

FIG. 1 shows the nucleic acid corresponding to the human testicular ACE and the polypeptide deduced from it;

FIG. 2 presents the respective positions of the nucleic acids of the four clones used for the determination of the nucleic acid coding for human testicular ACE.

A more detailed study of the nucleic acid of the invention as well as the polypeptide deduced from this latter and corresponding to human testicular ACE leads to the following observations:

the composite sequence of the cDNA of the testicular ACE is 2477 nucleotides long and is defined by the nucleotides corresponding to the positions 1 and 2477 of FIG. 1. The nucleotide sequence defined by the nucleotides situated at the positions 29 and 2224 of FIG. 1 contains an open reading frame coding for a polypeptide of 732 amino acids. This nucleotide sequence is constituted by a DNA sequence defined by the nucleotides corresponding to the positions 29 and 91 of FIG. 1 likely to code for a signal peptide of 21 amino acids and a DNA sequence defined by the nucleotides situated at the positions 92 and 2224 of FIG. 1, capable of coding for a mature protein of 711 amino acids;

the nucleotide sequence defined by the nucleotides situated at the positions 228 and 2224 of FIG. 1 is identical with that defined by the nucleotides situated at the positions 1944 to 3940 coding for the last 665 amino acids of the human endothelial ACE and shown in FIG. 2 of the article by SOUBRIER et al cited above;

the nucleotide sequence defined by the nucleotides situated at the positions 29 and 229 coding for the first 67 amino acids of the testicular pre-enzyme (or precursor of the testicular enzyme), and more particularly the sequence defined by the nucleotides situated at the positions 92 and 229 coding for the first 46 amino acids of the mature testicular enzyme are particularly specific for the testicular ACE;

the polypeptide comprising a sequence (SEQ ID NO. 3) His-Glu-Met-Gly-His corresponding to the amino acids situated at the positions 414 to 418 of FIG. 1 may constitute a part of the active site of the testicular ACE.

Hence, the present invention relates to any nucleic acid, characterized in that it comprises all or part of the nucleotide sequence of FIG. 1, this part itself comprising all or part of the nucleotide sequence defined by the nucleotides situated at the positions 29 and 229 of FIG. 1, and in that it codes for a polypeptide capable of being recognized by polyclonal or monoclonal antibodies specifically recognizing any peptide derived from the peptide sequence defined by the amino acids situated at the positions 1 to 67 of FIG. 1, and, where appropriate, capable of hydrolysing angiotensin I and/or kinins, in particular bradykinin, or any nucleic acid differing from the previous one with respect to its nucleotide sequence only by substitutions of nucleotides not leading to modification of the amino acid sequence of the above-mentioned polypeptide under conditions likely to cause it to lose the above-mentioned properties.

The invention relates more particularly to any nucleic acid comprising the DNA sequence defined by the nucleotides situated at the positions 29 and 2224 of FIG. 1, and coding for the human testicular pre-ACE (or pro-enzyme) of 732 amino acids; the first 21 amino acids at the N-terminus represent the signal peptide and the remaining 711 amino acids represent the mature human testicular ACE.

The invention also relates to any nucleic acid comprising the DNA sequence defined by the nucleotides situated at the positions 92 and 2224 of FIG. 1, and coding for the mature human testicular ACE.

Among the nucleic acids conforming to the invention, particular mention should be made of the one comprising a DNA sequence extending, on the one hand, from a nucleotide situated between the positions 1 to 92 and, on the other, a nucleotide situated between the positions 229 to 2224 of FIG. 1.

The object of the invention is more particularly any nucleic acid comprising the part of the nucleotide sequence of FIG. 1 which is specific for the testicular ACE, namely any nucleic acid containing the nucleotide sequence extending, on the one hand, from the nucleotide situated at the position 29, to, on the other, the nucleotide situated at the position 227 of FIG. 1, or any nucleic acid containing a sequence derived from this latter.

In this sense, the invention also relates to:

any nucleic acid comprising a DNA sequence of about 15, and preferably 45, to 201 nucleotides derived from the nucleotide sequence extending from the nucleotide situated at position 29 to the nucleotide situated at position 227 of FIG. 1, any nucleic acid comprising a DNA sequence of about 15, and preferably 45, to 135 nucleotides derived from the nucleotide sequence extending from the nucleotide at position 92 to the nucleotide situated at position 227 of FIG. 1.

The invention also relates to the nucleic acids derived from those mentioned above, the nucleotide sequences of which are modified within the limits allowed by the degeneracy of the genetic code, provided that the polypeptides encoded by these nucleic acids conserve either an identical primary structure or their immunological and where appropriate, enzymatic properties.

Such non-limiting modifications lead, for example, to nucleic acid variants which differ from the above nucleic acids, by addition and/or deletion of one or more nucleotides and/or modification of one or more nucleotides.

The object of the invention is more particularly any nucleic acid exhibiting the property of hybridizing specifically with the nucleic acid shown in FIG. 1, in particular under the conditions defined below:

denaturation of the nucleic acid (when it is in the double-stranded DNA form) capable of hybridizing with that of FIG. 1, before its attachment to the support, defined below, by treatment with the aid of an alkaline solution (0.5 M NaOH), followed by a return to neutral pH.

prehybridization treatment of the support (nitrocellulose filter or nylon membrane), to which is bound the nucleic acid capable of hybridizing with that of FIG. 1 at 50° C. for 3 hours with a solution having the following composition: 25 mM $KPO_4$, pH 7.4; 5×SSC; 5×Denhardt's; 50 µg/ml of sonicated salmon sperm DNA; 0.1% sodium dodecyl sulfate (SDS or NaDod $SO_4$), replacement of the pre-hybridization solution in contact with the support by a buffer solution having an identical composition with that of the pre-hybridization buffer indicated above (possibly with the addition of 10% Dextran) and containing the nucleic acid of FIG. 1 as a labelled probe, in particular as radioactive probe, and previously denatured by a treatment at 90° C. for 3 minutes, incubation for 12 hours at 60° C., successive washings with the following solutions:

2 washings with 2×SSC for 30 minutes at 60° C.,

1×SSC, 0.1% SDS once or twice for 15 minutes at 65° C.

It should be recalled that the composition of the Denhardt solution is the following: 1% Ficoll, 1% polyvinylpyrrolidone, 1% BSA (bovine serum albumin), and that 1×SSC is a solution containing 0.15 M of NaCl and 0.015 M of sodium citrate, pH 7.

The invention also relates to any nucleic acid exhibiting the property of hybridizing specifically with the nucleic acid of FIG. 1 under non-stringent conditions employing the essential characteristics of the stringent conditions defined above except the temperature which is 40° C. under non-stringent conditions, and the successive washings which, under non-stringent conditions, are performed twice with the aid of 2×SSC with or without SDS at 45° C. for 15 minutes.

The invention also relates to any nucleic acid capable of hybridizing with the nucleic acids derived from that of FIG. 1 such as those defined above or their complementary sequences, in particular under the conditions of hybridization described above.

The invention also relates to nucleotide probes capable of hybridizing with the entire length of the nucleic acid of FIG. 1, or with any fragment as defined above of this nucleic acid, as well as with the messenger RNA coding for the testicular ACE and with the human gene responsible for the expression of the testicular ACE, in particular under the conditions of hybridization defined above, or their complementary sequences.

It will be obvious that the stringent or non-stringent conditions of hybridization defined above constitute preferred conditions for the hybridization but are in no way limiting and may be modified without in any way affecting the properties of recognition and hybridization of the probes and nucleic acids mentioned above.

The salt conditions and the temperature during the hybridization and the washing of the membranes may be modified in the sense of a greater or lesser stringency without the detection of the hybridization being affected. For example, it is possible to add a variable percentage of formamide in order to lower the temperature during the course of hybridization.

The invention also relates to the polypeptide of FIG. 1 corresponding to human testicular ACE as well as all of the polypeptides encoded by the above-mentioned DNA fragments derived from the nucleic acid of FIG. 1, capable of being recognized by polyclonal or monoclonal antibodies specifically recognizing any peptide derived from the peptide sequence defined by the amino acids situated at the positions 1 to 67 of FIG. 1, and more particularly that defined by the amino acids situated at the positions 22 to 67 of FIG. 1 and, where appropriate, of possessing an enzymatic activity of the testicular ACE type.

Among the above-mentioned polypeptides, the following should be singled out:

- the polypeptide extending between the amino acids corresponding to the positions 1 and 732 of FIG. 1;
- the polypeptide extending between the amino acids corresponding to the positions 22 and 732;
- the polypeptide, the peptide sequence of which is defined by the amino acids situated at the positions 1 and 67 of FIG. 1,
- the polypeptide, the peptide sequence of which is defined by the amino acids situated at the positions 22 and 67 of FIG. 1, p1 the polypeptide characterized by the peptide sequence of about 5 to 67 amino acids, derived from the peptide sequence defined by the amino acids situated at the positions 1 and 67 of FIG. 1,
- the polypeptide characterized by the peptide sequence of about 5 to 45 amino acids, derived from the peptide sequence defined by the amino acids situated at the positions 22 and 67 of FIG. 1.

The polypeptides just mentioned may be modified provided that they conserve the biochemical or immunological or pharmacological properties previously defined.

For example, and in a non-limiting manner, polypeptides in the context of the invention may differ from the polypeptides defined above:

- by addition and/or
- deletion of one or more amino acids and/or
- modification of one or several amino acids, provided that the biochemical or immunological or pharmacological properties as defined above are conserved.

It may be taken for granted that the person skilled in the art will have the means to identify, and even select, those polypeptides with shorter sequences which enter into the framework of the invention. As an example of one of the general means which enable him to carry out this identification, mention should be made, for example, of the treatment of the polypeptide of FIG. 1 with a protease which cleaves the above-mentioned polypeptide at a selected site either in the N-terminal region or in the C-terminal region, followed by the separation of the N-terminal fragment or the C-terminal fragment from the rest of the said polypeptide, this "remainder" being then tested for its properties of recognition by the monoclonal or polyclonal antibody directed against a peptide derived from the peptide sequence defined by the amino acids situated at the positions 22 to 67 of FIG. 1, and, where appropriate, for its enzymatic activity towards angiotensin and/or bradykinin. In the case of a positive response, it will then have been established that the N-terminal or C-terminal fragment plays neither a significant nor essential role in the expression of the immunological and/or enzymatic properties of the said polypeptide. If required, the operation may be repeated provided that a protease is available which is capable of recognizing another specific site close to the N-terminus or C-terminus of the remaining polypeptide. The loss by the shorter polypeptide of the immunological and/or enzymatic properties recognized in the longer fragment from which it was derived may lead to the hypothesis that the latter separated fragment plays a significant role in the expression of the enzymatic properties of the polypeptide of FIG. 1.

Another variant, simpler that the previous one, for the detection of the regions of the testicular ACE essential for the expression of the enzymatic properties of this latter may be based on enzymatic treatments of a nucleic acid coding for the testicular ACE. This treatment is carried out before the incorporation of the nucleic acid thus obtained, and presumed to code for a polypeptide possessing immunological and/or enzymatic activities characteristic of the testicular ACE, in the expression vector used for the implementation of a procedure for the production of the said polypeptide in a suitable cell host (a procedure which will be described in more detail in what follows). This enzymatic treatment may then consist either of a trimming of the ends of the original nucleic acid (coding, for example, for the entire polypeptide of FIG. 1) for example by means of an exonucleolytic enzyme such as Bal31, or by means of one or more restriction enzymes selected for their respective recognition sites (modified, if necessary by site-specific mutagenesis) in the sequence of the original nucleic acid, or by the addition of a fragment of synthetic DNA linking the cleavage site of the restriction enzyme to the start of the region to be expressed. In this way, sequences of increasing lengths may be deleted from the 3' end of the messenger RNA and replaced by a translation stop codon. The same approach may be applied to the 5' end but requires that an initiation codon (ATG), the signal peptide or any other sequence permitting the secretion of the peptide and the open reading frame be maintained intact.

After incorporation into the selected vector and transformation of the cell host with the recombinant vector obtained, the truncated nucleic acid obtained may then be tested for its capacity to express a corresponding truncated polypeptide still possessing the above-mentioned immunological and/or enzymatic properties or, on the contrary, no longer possessing them, as a consequence of which as in the former variant, it is possible to identify within the polypeptide of FIG. 1 the sequences which play an important, if not essential, role in the expression of the immunological and/or enzymatic properties of the testicular ACE.

Another object of the invention is any recombinant nucleic acid containing any DNA fragment of the type mentioned above coding for the human testicular pre-ACE, or the mature human testicular ACE, or also for any polypeptide likely to possess an immunological and/or enzymatic activity characteristic of the testicular ACE, linked to a promoter and/or terminator of transcription recognized by the polymerases of the cell host into which the said recombinant nucleic acid is likely to be introduced.

The introduction of the said recombinant nucleic acid into the cell host is advantageously performed with the aid of vectors, in particular of the plasmid type, which are capable of replicating in the said cell host and of giving rise in it to the expression of the sequence coding for the enzyme.

The said recombinant nucleic acid may also be introduced in the cell host with the aid of a viral vector (recombinant virus) capable of infecting the said cell host, or with the aid of a retroviral vector capable of being integrated into the genome of the cell host, and of giving rise in it to the expression of the polypeptide encoded by a nucleic acid according to the invention, this latter being under the control of a viral or retroviral promoter, active in the cell host.

As examples of vectors which can be used in the framework of the invention, mention should be made of the Moloney murine leukaemia virus (M-MuLV) capable of infecting NIH 3T3 cells, or the baculovirus used to infect insect cells.

Hence, the invention relates to a process for the production of the human testicular ACE, or the above-mentioned polypeptides derived from the testicular ACE, which comprises the transformation of the host cells by means of the above-mentioned vectors, the placing in culture of the transformed host cells in a suitable medium and the recovery of the said polypeptides either directly from the culture medium when these latter are secreted into it (particularly in the case in which the polypeptides under consideration are preceded by a signal sequence at the time of their synthesis in the host cell), or after lysis of the wall of the cell host in the case in which the polypeptides are not secreted outside of the latter.

The host cells used for the implementation of the above-mentioned procedure may be procaryotic cells, in particular E.coli cells, or more advantageously, eucaryotic cells which make it possible, in particular, to obtain proteins in their mature and glycosylated form (yeasts, CHO cells, or insect cells infected with baculovirus).

The invention also relates to a process for the preparation of the novel peptides mentioned above by syntnesis which comprises either the stepwise addition of the selected amino acid residues one at a time, with the additional removal of whatever groups are used for the protection of the amino and carboxyl functions, or the addition of selected amino acid residues in order to produce fragments, followed by condensation of the said fragments to form a suitable sequence of amino acids, with the addition or removal of the selected protecting groups.

The invention also relates to specific antibodies directed against the above polypeptides. In particular, the invention relates to polyclonal or monoclonal antibodies directed against the above-mentioned peptide sequences.

One method of preparing polyclonal antibodies against a peptide derived from the sequence of the testicular ACE is briefly summarized below:

the peptide, the minimal size of which is about 5 to 15 amino acids, is coupled either to bovine serum albumin or KLH (Keyhole Limpet Hemocyanin (Megathura crenulata)) if the peptide contains a cysteine, which may be added artificially to the natural sequence. This cysteine will have previously been activated by SPDP=N-hydroxysuccinimide ester of 3-(2-pyridyldithio) propionic acid, or with KLH or LPH (hemocyanin of the hemolymph of Limulus polyhemas) through the intermediary of benzoquinone;

or to LPH by means of glutaraldehyde, or to LPH by means of carbodiimide the coupled peptide is then injected in an equal volume of Freund's adjuvant into the foot pad of the hind paw of rabbits. At the time of the first injection, complete Freund's adjuvant is used.

Subsequently, incomplete adjuvant is employed, a booster injection is given every 3 to 4 weeks, between each injection, a blood sample is taken to measure the antibody titer (the antibody titer is established by measuring the dilution at which 50% of the peptide which has been used in the injections and which is radioactively labelled is bound to the antibody).

The above-mentioned monoclonal antibodies may be produced by the hybridoma technique, the general principle of which is given below.

In the first step, one of the above polypeptides is inoculated into a selected animal (for example, mouse of the type Biozzi or Balb/C), whose B lymphocytes are then capable of producing antibodies against this polypeptide. The injection protocol consists, for example, of three injections, the first of which is given with complete Freund's adjuvant. The animals may receive an I.V. injection of the polypeptide several hours before the isolation of the spleen cells. The spleen cells of the animal having received the injection are then fused with "immortal" myeloma cells according to the method described by DI PAULI (DI PAULI R. and W. C. RASCHKE, (1978), in Current Topics in Micro-biology and Immunology, vol. 81, F. MELCHERS, M. POTTE, and N. L. WARNER, editors, Springer-Verlag, Berlin, 37–39), with the aid of polyethylene glycol. The cells which have fused (hybridomas) are then placed in culture and selected in a hypoxanthine-aminopterine-thymidine medium. Starting from the heterogeneous mixture of the cells thus obtained, a selection is then made of the cells capable of producing a specific antibody and of allowing them to multiply indefinitely.

The hybridomas producing antibodies are then cloned and sub-cloned with the aid of a cell sorter. The hybridomas are then reinjected into the peritoneum of animals, in particular Balb/C mice treated with pristane. The ascites are then tested for the presence of antibody and the immunoglobulins present in the ascites are purified on an affinity column, in particular on protein A-Sepharose.

Mono or polyclonal antibodies may also be produced against the entire ACE molecule.

Among the polypeptides used for the production of the above-mentioned monoclonal or polyclonal antibodies, special mention should be made of the specific polypeptides of the testicular ACE, namely those defined by the amino acids situated at the positions 1 and 67, or 22 and 67 of FIG. 1, or also those possessing at least 5 amino acids derived from the peptide sequence defined by the amino acids situated at the positions 1 and 67 of FIG. 1.

The invention also relates to an in vitro screening or assay method for ACE or for a product having in vivo the properties of the ACE, and more particularly of the human testicular ACE, or of a product derived from the testicular ACE such as the polypeptide mentioned above, in a biological sample likely to contain them. Such a screening method according to the invention can be set up either with the aid of the above-mentioned monoclonal antibodies, or with the aid of the nucleotide probes described above.

The invention relates more particularly to the use of the monoclonal or polyclonal antibodies obtained starting from the peptide defined by the amino acids situated at the positions 1 and 67, or the one defined by the amino acids situated at the positions 22 and 67, or also the one derived from the peptide sequence defined by the amino acids situated at the positions 1 and 67 of FIG. 1, and specifically recognizing these polypeptides, for the implementation of an in vitro screening or assay method for the human testicular ACE.

The invention also relates to the use of the nucleotide probes described above, in particular those hybridizing with the nucleic acid sequences coding for the specific polypeptides of the human testicular ACE described above for the implementation of the above-mentioned screening or assay method.

The above-mentioned biological sample is taken from body fluids such as the blood or from organ tissues, this latter type of sample making it possible to prepare fine slices of tissue to which the above-mentioned antibodies or probes are subsequently bound.

The assay method according to the invention, being carried out through the intermediary of the above-mentioned antibodies, comprises in particular the following steps:

the placing in contact of an antibody recognizing specifically the testicular ACE or a polypeptide derived from the testicular ACE according to the invention, with the above-mentioned biological sample under conditions leading to the possible production of an immunological complex formed between the testicular ACE or product which is derived from it and the above-mentioned antibody;

the detection of the above-mentioned immunological complex with the aid of any appropriate means.

Advantageously, the antibodies used for the implementation of such a procedure are labelled, in particular enzymatically or radio-actively.

Such a method according to the invention can in particular be carried out according to the ELISA (enzyme linked sorbent assay) method which comprises the following steps:

binding of a predetermined quantity of antibody to a solid support, in particular to the surface of a well of a microplate;

addition of the biological sample (in liquid form) to the said support;

incubation for a time sufficient to allow the immunological reaction between the said antibodies and the testicular ACE or the above-mentioned product which is derived from it to take place;

removal of the unbound parts of the biological sample and washing of the solid support (in particular, the wells of the microplate);

addition of an immunoglobulin labelled by an enzyme capable of activating a specific substrate of the enzyme, addition of the substrate specific for the enzymatic activity released during the preceding immunological reaction;

detection of the degradation of the substrate by the enzyme by any appropriate means; and correlation of the amount of enzymes liberated with the concentration of human ACE initially present in the biological sample.

According to another embodiment of the assay method of the invention, the above-mentioned antibodies are not labelled and the detection of the immunological complexes formed between the polypeptides and the said antibodies is achieved with the aid of a labelled immunoglobulin recognizing the said complexes.

The assay method according to the invention can also be carried out by an immuno-enzymatic technique depending on a competition mechanism between the polypeptides likely to be contained in the biological sample and predetermined amounts of these same polypeptides for the above-mentioned antibodies. In this latter case, a predetermined quantity of the polypeptides of the invention is advantageously labelled with the aid of an enzymatic marker.

The invention is in no way limited to the embodiments described above for the in vitro assay of the polypeptides of the invention, since this assay can be carried out with the aid of any other suitable immunological method.

The invention also relates to an in vitro screening or assay method for an ACE or a product having in vivo the properties of the ACE and, more particularly, of human testicular ACE, this method consisting of the detection or assay of a nucleic acid corresponding according to the universal genetic code to all or part of this ACE, and being carried out starting from a biological sample likely to contain the said nucleic acid. This method is characterized in that it comprises:

the placing of a nucleotide probe described above in contact with the above-mentioned biological sample under conditions leading to the possible production of a hybridization complex formed between the nucleic acid to be detected and the said probe;

the detection of the above-mentioned hybridization complex with the aid of any suitable agent.

According to one embodiment of the invention, the above-mentioned biological sample is treated, prior to the screening, in a manner such that the cells which it contains are lysed and, where appropriate, in that the genomic material contained in the said cells is fragmented with the aid of restriction enzymes of the type EcoRI, BamHI, etc. . ., or in that the RNAs are isolated from them, in particular according to the method described in THOMAS, P. S. (1983) *Methods Enzymol.*, 100, 255–266.

Advantageously, the nucleotide probes of the invention are labelled, in particular by the incorporation of a nucleotide (or several) which is either radioactive or coupled to a hapten making possible its detection by an antibody, this latter being conjugated to an enzyme, the activity of which can easily be detected (for example, alkaline phosphatase). The DNAs or RNAs derived from the biological sample are placed on a suitable support, in particular a nitrocellulose or other type of filter, for example nylon membrane, to which the above-mentioned probes are then added.

According to another advantageous embodiment of the above-mentioned procedure of the invention, histological slices are prepared from the above-mentioned biological sample and the nucleotide probes of the invention are placed in direct contact with the histological slices for the detection of the nucleic acids of the invention by in situ hybridization.

The invention also relates to the use of the screening or assay method for the testicular ACE mentioned above for in vitro diagnoses of specific diseases of the testicles (in particular, of the germ cells), in particular tumors of the testicles (also called seminomas), the maturation of the male germ cells, hypofertility and male sterility.

In the context of the diagnosis of hypofertility and masculine sterility, the above-mentioned method is advantageously carried out on sperm, or on germ cells or seminal plasma isolated from the sperm or on a testicular biopsy.

The invention also relates to kits for the implementation of the in vitro screening or assay methods mentioned above. As an example, such kits include in particular:

a defined quantity of one of the above-mentioned polyclonal or monoclonal antibodies capable of giving rise to a specific immunological reaction with the testicular ACE or with one of the polypeptides derived from the testicular ACE according to the invention:

and/or a defined quantity of testicular ACE or polypeptide capable of giving rise to an immunological reaction with the above-mentioned antibodies;

advantageously, a medium suitable for the occurrence of an immunological reaction between the ACE or the polypeptides of the invention and the above-mentioned antibodies;

advantageously, reagents making possible the detection of the immunological complexes produced as a result of the above-mentioned immunological reaction.

In the context of the implementation of an in vitro screening method using nucleotide probes, the kits used contain for example:

a defined quantity of one of the above-mentioned nucleotide probes capable of giving rise to a hybridization reaction with one of the above-mentioned nucleic acids coding for the testicular ACE or a polypeptide derived from the testicular ACE according to the invention;

advantageously, reagents leading to the detection of the hybridization complexes produced during the above-mentioned hybridization reaction.

The invention also relates to the use of the polypeptide of FIG. 1 or any suitable peptide fragment derived from this latter for the design of new inhibitors of the human ACE, more powerful and/or specific towards this latter than are the current inhibitors of the ACE.

The invention also relates to a method for the detection or assay of an inhibitor of the ACE, or for the quantification of its inhibitory potency, which comprises the placing of the polypeptide of FIG. 1 or of any peptide fragment derived from the latter and possessing an enzymatic activity characteristic of the ACE in contact with the said inhibitor, and the determination of the dissociation constant (Ki) and the concentration necessary to inhibit 50% of the enzyme ($IC_{50}$) for these inhibitors.

The invention also relates to the utilization of the polypeptide of FIG. 1, or of any fragment of this latter such as described above capable of hydrolysing the kinins, in particular bradykinin, in the treatment of inflammatory or infectious diseases, acute pancreatitis, and more generally, diseases in which the release of kinins into the organism may play a pathogenic role.

Therefore, the invention relates more particularly to pharmaceutical compositions for the treatment of the diseases indicated above, characterized by the combination of all or part of the polypeptide of FIG. 1, which is capable of hydrolysing the kinins, in particular bradykinin, with a pharmaceutically acceptable vehicle.

The present invention also relates to the use of the nucleotide probes of the invention, which are capable of hybridizing with the gene responsible for the expression of the human testicular ACE under the conditions described above, for the determination of the different allelic forms of the above-mentioned gene.

The invention also relates to any nucleotide sequence of about 15 to about 30 nucleotides derived from the nucleotide sequence of FIG. 1, or a sequence complementary to this latter, or also a sequence of about 15 to 30 nucleotides capable of hybridizing (under the conditions described above) with the said sequence of about 15 to 30 nucleotides derived from FIG. 1, and the utilization of such sequences as primers making possible the genic amplification of all or part of the nucleotide sequence of FIG. 1, in particular according to the method of amplification described in the European patent application No. 86/302.298.4 of 27/03/1986.

These oligonucleotide primers are particularly useful in the context of the synthesis of the testicular ACE by means of the genetic engineering approach such as that described above, the different steps of which mentioned above are preceded by an amplification step of the gene coding for the testicular ACE, prior to the transformation step of the host cells.

The invention also relates to an in vitro method for the detection of the mRNA coding for the testicular ACE, such as that described above, comprising a prior step of amplification of all or part of this mRNA (or the amplification of the DNA copy of the RNA coding for the testicular ACE), if necessary, isolated from the other cell constituents, with the aid of one or more primer couples such as described above.

Consequently, the invention also relates to diagnostic kits such as those described above, also containing at least one of the above-mentioned primer couples, these primers being capable of amplifying the number of copies of the nucleic acid to be detected in the presence of a suitable polymerase and appropriate quantities of the 4 different deoxynucleotide triphosphates, dATP, dGTP, dCTP and dTTP.

Additional characteristics of the invention will also become apparent during the course of the description which follows of the cloning of the nucleic acid coding for human testicular ACE as well as the probes used for this cloning, it being understood that this description is not to be interpreted as tending to limit the scope of the claims.

SEQUENCING OF THE COMPLEMENTARY DNA OF HUMAN TESTICULAR ACE

A library of cDNAs of human testicles primed with oligo(dT), constructed in the phage λgt11 (Clontech laboratories Inc.) was screened using the probe described below.

The hybridizations with the phages were performed according to the method of Benton W. D. and Davis R. W., *Science* (WASHINGTON), 1977, 196, 180–182. More exactly, the hybridizations were performed in a solution constituted of 6×SSC (1×SSC corresponds to 150 mM NaCl, 15 mM sodium citrate), 0.1% of $NaDodSO_4$, 50 mM $NaPO_4$ buffer at pH 6.8, 0.1 mg/ml of denatured salmon sperm DNA at 65° C.

The sequence used as probe is contained in the bacteriophage λ19–22 and represents the last 3248 nucleotides of the complementary DNA sequence (positions 691 to 4024), as described in the article by SOUBRIER F. et al., mentioned above. It was chosen because it hybridizes with the messenger RNA of the ACE of the human testicle. The cloned sequence of the DNA of the endothelial ACE was used as probe, using statistical labelling with the aid of the DNA polymerase I of *E. coli* and oligonucleotide primers according to the method described by FEINBERG A. P. et al. (1983), *Anal. Biochem.*, 132, 6–13. By using alpha $\beta^{32}P$/deoxycytidine triphosphate with a specific activity of 3000 cies/mmole, the probe has a specific activity of 2 to $8\times10^9$ cpm/μg of DNA. The concentration of the radioactive probe in the hybridization solution for the filters is $10^6$ cpm/ml. The filters were then washed under conditions of high stringency (final washing with 0.1×SSC, 0.1% $NaDodSO_4$) at 68° C. for 30 minutes. The screening of $2\times10^6$ clones of the library made it possible to isolate 17 positive clones. Two positive clones were isolated from these latter. The DNA fragments inserted into the recombinant phages were purified and inserted into the EcoRI site of the plasmid Bluescript (Stratagene). The sequence of the insertions was determined either directly on the double-stranded DNA of the plasmids, or on the single-stranded DNA by infecting the cultures with the aid of the helper phage K07.

The determination of the nucleotide sequence of these clones was carried out by the method of Sanger (SANGER, F. et al (1977), *Proc. Natl. Acad. Sci.*, USA, 74, 5463–5467) by using either the Klenow DNA polymerase or the modified DNA polymerase of T7 (Sequenase, US Biochemical). Some regions were sequenced by using deoxyinosine triphosphate (dITP) or deaza-deoxyguanosine triphosphate (7-deaza dGTP) instead of deoxyguanosine triphosphate (dGTP). The electrophoresis of the fragments labelled with $S^{35}$ dATP was carried out on a urea-polyacrylamide gel. The sequences were determined by synthesizing, step by step about every 350 base pairs, oligomers which served as primers placed at intervals throughout the entire sequence.

The clone λht10 contains a sequence 2217 nucleotides long which extends from position 260 to position 2477 of the sequence of the testicular cDNA shown in FIG. 1. The clone extends into the 3' region of the messenger RNA up to the polyadenylation sequence and includes a short poly(A) sequence. The clone λht16, 2263 nucleotides long, corresponds to the region of the testicular cDNA situated between position 50 and position 2313 of FIG. 1. An oligomer 22 nucleotides long was synthesized and used to screen the library again in order to obtain clones corresponding to the region closest to the 5' end of the messenger RNA. The sequence of this oligomer is contained in the sequence of the clone λht16 (positions 59 to 80). The oligomer was labelled with γ-/$^{32}$P/ adenosine triphosphate ATP (specific activity 5000 cies/mmoles) with the aid of the T4 polynucleotide kinase. The specific activity of the probe is $5 \times 10^6$ cpm/pmole. The filters were screened under the same conditions as specified above except for the following modifications: the hybridization temperature was 60° C. and the washing was done at a temperature of 65° C. in a 2×SSC solution. This screening made it possible to isolate the clone λht341, 2.2 kb long, which extends from the 5' to nucleotide 31 of the testicular cDNA of the ACE.

In order to obtain the complementary DNA corresponding to the 5' end of the messenger RNA coding for the testicular ACE, another cDNA library was constructed by using 5 μg of RNA isolated from human testicular tissue obtained during a surgical operation. The complementary DNA library was constructed according to the method of G übler and Hoffman (Gene (1983), 25, 263–269) by using two primers. The first is a specific primer for the messenger RNA of the ACE, determined by the sequence of the clones previously obtained. It is an oligomer of 17 bases (ATH17), complementary to a sequence located at positions 228–244 of FIG. 1. The second primer corresponds to the oligo d(T)12–18 mers (Pharmacia). The double-stranded complementary DNAs were synthesized, then inserted into the phage λgt10 cut by the enzyme EcoRI according to the method of Koenig et al (Koenig, M. et al. (1987), Cell, 50, 509–517).

The recombinant phages ($1 \times 10^6$ recombinant phages) were screened with the aid of the oligomer TH16, labelled as before. The conditions for screening the library are identical with those described above with the same probe. Of the positive clones obtained, the clone λht221, 244 base pairs long, was sequenced. It contains the part closest to the 5' end of the messenger RNA coding for the testicular ACE.

The sequence of the testicular messenger RNA, as may be deduced from the composite nucleotide sequence of the testicular cDNA obtained starting from the 4 clones, is 2477 nucleotides long. It exhibits an identical nucleotide sequence with that of the endothelial messenger RNA on the 3' side of the position 228 of the testicular cDNA. On the 5' side of this position the testicular and endothelial messenger RNAs differ and the established testicular specific sequence is 228 nucleotides long. From the first ATG codon up to the stop codon there exists an open reading frame coding for 732 amino acids. The analysis of the peptide sequence deduced from the nucleotide sequence shows that after the starting methionine of translation there exists a peptide which exhibits the properties of a signal peptide and by using the program described by VON HEIJNE (Nucleic Acids Research, (1986), 14, 4683–4690) for the prediction of cleavage sites for a signal peptide, the cleavage site for the signal peptide should be situated between the amino acid at position 21 and that at position 22. After this signal sequence, the peptide sequence specific for the testicular ACE is very rich in serine and threonine, potential glycosylation sites, and this type of sequence is suggestive of O-glycosylation clusters.

Since the enzymatic properties of the testicular enzyme are identical with those of the endothelial enzyme, particularly with respect to the Km, the Vmax and Kcat, towards anoiotensin I, the comparison of its structure with that of the endothelial enzyme provides interesting information concerning the structure/activity relationships in the ACE molecule. In fact, the endothelial enzyme is constituted of two large domains, very homologous with each other. Each of these domains contains a short consensus sequence of amino acids characteristic of the active site of the zinc metallopeptidases such as thermolysin collagenase or neutral endopeptidase. The testicular converting enzyme contains only the carboxyterminal domain of the endothelial ACE which seems to indicate that this domain alone bears the structures responsible for the enzymatic activity. Another hypothesis would be that the testicular enzyme acts in the form of a dimer, however the native testicular enzyme of the rabbit tested under non-denaturing conditions by means of density gradient centrifugation definitely has a lower molecular weight than that of the endothelial ACE.

We claim:

1. An isolated and purified nucleic acid containing a human sequence encoding human testicular angiotensin converting enzyme consisting of the nucleotide sequence of SEQ ID NO: 1, or a part of this sequence comprising about 15 to 201 nucleotides of positions 29 to 229 of SEQ ID NO: 1 which encodes for a polypeptide, wherein said polypeptide is recognized by polyclonal or monoclonal antibodies recognizing specifically any peptide corresponding to the peptide sequence of positions 1 to 67 of SEQ ID NO: 2.

2. An isolated and purified nucleic acid consisting of a human sequence coding for testicular angiotensin converting enzyme which hybridizes with the nucleic acid sequence of nucleotides 1 to 229 of SEQ ID NO: 1 under stringent conditions of hybridization, wherein said stringent conditions comprise the following:

hybridization in a solution comprising: 25 mM $KPO_4$, 5X SSC, 5X Denhardt's, 50 µg/ml sonicated salmon sperm DNA, and 0.1% sodium dodecyl sulfate at about 60° C.; and washing in a solution comprising 2X SSC at 60° C. and in a solution comprising 1X SSC and 0.1% SDS at about 65° C.

3. An isolated and purified nucleic acid consisting of a DNA sequence of positions 92 to 2224 of SEQ ID NO: 1, coding for mature human testicular angiotensin converting enzyme.

4. An isolated and purified nucleic acid consisting of a nucleic acid of claim 3 preceded by a DNA sequence consisting of positions 29 to 91 of SEQ ID NO: 1 encoding a signal peptide of 21 amino acids.

5. The nucleic acid according to claim 1, consisting of the DNA sequence of positions 29 to 229 of SEQ ID NO: 1.

6. A polypeptide encoded by the nucleic acid according to claim 1, wherein the peptide sequence comprises the amino acids between positions 1 to 67 of SEQ ID NO: 2.

7. A polypeptide encoded by the nucleic acid according to claim 1, wherein the peptide sequence comprises the amino acids between positions 22 to 67 of SEQ ID NO: 2.

8. A polypeptide encoded by the nucleic acid according to claim 1, wherein the peptide sequence comprises the amino acids between positions 1 to 67 of SEQ ID NO: 2, or a fragment thereof of about 5 to 67 amino acids.

9. A polypeptide encoded by the nucleic acid according to claim 1, wherein the peptide sequence comprises the amino acids between positions 22 to 67 of SEQ ID NO: 2, or a fragment thereof of about 5 to 45 amino acids.

10. A nucleic acid consisting of the nucleic acid of claim 1 linked to:

a promoter under the control of which the transcription of said nucleic acid of claim 1 is effected; and a DNA sequence coding for transcription termination signals.

11. A recombinant vector, capable of transforming or infecting a suitable host cell, said vector containing a nucleic acid according to claim 1 under the control of regulatory elements making possible the expression of this DNA fragment in the host cell.

12. A polyclonal or monoclonal antibody, which specifically recognizes any peptide corresponding to the peptide sequence of positions 1 to 67 of SEQ ID NO: 2.

13. A kit for the implementation of an in vitro screening method comprising:

a defined quantity of an antibody according to claim 12 capable of giving rise to an immunological reaction with a polypeptide to be detected;

a medium capable of forming an immunological reaction between the polypeptide and antibody; and reagents for detection of the immunological complexes formed between the polypeptide and the antibody during the immunological reaction.

* * * * *

UNITED STATES PATENT AND TRADEMARK OFFICE
CERTIFICATE OF CORRECTION

PATENT NO.: 5,801,040

DATED: September 1, 1998

INVENTOR(S): Florent SOUBRIER, François ALHENC-GELAS, Christine HUBERT, and Pierre CORVOL, It is certified that an error appears in the above-identified patent and that said Letters Patent is hereby corrected as shown below:

Title page [75] Inventors: add "Pierre Corvol, Paris, France"

Signed and Sealed this

Twentieth Day of March, 2001

Attest:

NICHOLAS P. GODICI

*Attesting Officer*     *Acting Director of the United States Patent and Trademark Office*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 2478 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
AGCTGCAGGA CTCTGCTCTC CTGCGGCCAT GGGCCAGGGT TGGGCTACTG CAGGACTTCC      60

CAGCCTCCTC TTCCTGCTGC TCTGCTACGG GCACCCTCTG CTGGTCCCTA GCCAGGAGGC     120

ATCCCAACAG GTGACAGTCA CCCATGGGAC AAGCAGCCAG GCAACAACCA GCAGCCAGAC     180

AACCACCCAC CAGGCGACGG CCCACCAGAC ATCAGCCCAG AGCCCAAACC TGGTGACTGA     240

TGAGGCTGAG GCCAGCAAGT TTGTGGAGGA ATATGACCGG ACATCCAGG TGGTGTGGAA      300

CGAGTATGCC GAGGCCAACT GGAACTACAA CACCAACATC ACCACAGAGA CCAGCAAGAT     360

TCTGCTGCAG AAGAACATGC AAATAGCCAA CCACACCCTG AAGTACGGCA CCCAGGCCAG     420

GAAGTTTGAT GTGAACCAGT TGCAGAACAC CACTATCAAG CGGATCATAA AGAAGGTTCA     480

GGACCTAGAA CGGGCAGCGC TGCCTGCCCA GGAGCTGGAG GAGTACAACA AGATCCTGTT     540

GGATATGGAA ACCACCTACA GCGTGGCCAC TGTGTGCCAC CCGAATGGCA GCTGCCTGCA     600

GCTCGAGCCA GATCTGACGA ATGTGATGGC CACATCCCGG AAATATGAAG ACCTGTTATG     660

GGCATGGGAG GGCTGGCGAG ACAAGGCGGG GAGAGCCATC CTCCAGTTTT ACCCGAAATA     720

CGTGGAACTC ATCAACCAGG CTGCCCGGCT CAATGGCTAT GTAGATGCAG GGACTCGTG     780

GAGGTCTATG TACGAGACAC CATCCCTGGA GCAAGACCTG GAGCGGCTCT TCCAGGAGCT     840

GCAGCCACTC TACCTCAACC TGCATGCCTA CGTGCGCCGG GCCCTGCACC GTCACTACGG     900

GGCCCAGCAC ATCAACCTGG AGGGGCCCAT TCCTGCTCAC CTGCTGGGGA ACATGTGGGC     960

GCAGACCTGG TCCAACATCT ATGACTTGGT GGTGCCCTTC CCTTCAGCCC CCTCGATGGA    1020

CACCACAGAG GCTATGCTAA AGCAGGGCTG GACGCCCAGG AGGATGTTTA AGGAGGCTGA    1080

TGATTTCTTC ACCTCCCTGG GGCTGCTGCC CGTGCCTCCT GAGTTCTGGA ACAAGTCGAT    1140

GCTGGAGAAG CCAACCGACG GCGGGAGGT GGTCTGCCAC GCCTCGGCCT GGGACTTCTA    1200

CAACGGCAAG GACTTCCGGA TCAAGCAGTG CACCACCGTG AACTTGGAGG ACCTGGTGGT    1260

GGCCCACCAC GAAATGGGCC ACATCCAGTA TTTCATGCAG TACAAAGACT TACCTGTGGC    1320

CTTGAGGGAG GGTGCCAACC CCGGCTTCCA TGAGGCCATT GGGGACGTGC TAGCCCTCTC    1380

AGTGTCTACG CCCAAGCACC TGCACAGTCT CAACCTGCTG AGCAGTGAGG GTGGCAGCGA    1440

CGAGCATGAC ATCAACTTTC TGATGAAGAT GGCCCTTGAC AAGATCGCCT TTATCCCCTT    1500

CAGCTACCTC GTCGATCAGT GGCGCTGGAG GGTATTTGAT GGAAGCATCA CCAAGGAGAA    1560

CTATAACCAG GAGTGGTGGA GCCTCAGGCT GAAGTACCAG GGCCTCTGCC CCCAGTGCC     1620

CAGGACTCAA GGTGACTTTG ACCCAGGGGC CAAGTTCCAC ATTCCTTCTA GCGTGCCTTA    1680

CATCAGGTAC TTTGTCAGCT TCATCATCCA GTTCCAGTTC CACGAGGCAC TGTGCCAGGC    1740

AGCTGGCCAC ACGGGCCCCC TGCACAAGTG TGACATCTAC CAGTCCAAGG AGGCCGGGCA    1800

GCGCCTGGCG ACCGCCATGA AGCTGGGCTT CAGTAGGCCG TGGCCGGAAG CCATGCAGCT    1860

GATCACGGGC CAGCCCAACA TGAGCGCCTC GGCCATGTTG AGCTACTTCA AGCCGCTGCT    1920

GGACTGGCTC CGCACGGAGA ACGAGCTGCA TGGGGAGAAG CTGGGCTGGC CGCAGTACAA    1980

CTGGACGCCG AACTCCGCTC GCTCAGAAGG GCCCCTCCCA GACAGCGGCC GCGTCAGCTT    2040

CCTGGGCCTG GACCTGGATG CGCAGCAGGC CCGCGTGGGC CAGTGGCTGC TGCTCTTCCT    2100

GGGCATCGCC CTGCTGGTAG CCACCCTGGG CCTCAGCCAG CGGCTCTTCA GCATCCGCCA    2160

CCGCAGCCTC CACCGGCACT CCCACGGGCC CCAGTTCGGC TCCGAGGTGG AGCTGAGACA    2220

CTCCTGAGGT GACCCGGCTG GGTCGGCCCT GCCAAGGGC CTCCACCAG AGACTGGGAT      2280

GGGAACACTG GTGGGCAGCT GAGGACACAC CCCACACCCC AGCCCACCCT GCTCCTCCTG    2340

CCCTGTCCCT GTCCCCCTCC CCTCCCAGTC CTCCACCACC AGCCGCCCCA GCCCCTTCTC    2400
```

```
CCAGCACACG GCTGCCTGAC ACTGAGCCCC ACCTCTCCAA GTCTCCCTGT GAATACAATT    2460

AAAGGTCCTG CCCTCCCA                                                  2478
```

( 2 ) INFORMATION FOR SEQ ID NO:2:

( i ) SEQUENCE CHARACTERISTICS:
        ( A ) LENGTH: 732 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Gly Gln Gly Trp Ala Thr Ala Gly Leu Pro Ser Leu Leu Phe Leu
 1               5                  10                  15
Leu Leu Cys Tyr Gly His Pro Leu Leu Val Pro Ser Gln Glu Ala Ser
              20                  25                  30
Gln Gln Val Thr Val Thr His Gly Thr Ser Ser Gln Ala Thr Thr Ser
             35                  40                  45
Ser Gln Thr Thr Thr His Gln Ala Thr Ala His Gln Thr Ser Ala Gln
     50                  55                  60
Ser Pro Asn Leu Val Thr Asp Glu Ala Glu Ala Ser Lys Phe Val Glu
65                  70                  75                  80
Glu Tyr Asp Arg Thr Ser Gln Val Val Trp Asn Glu Tyr Ala Glu Ala
                 85                  90                  95
Asn Trp Asn Tyr Asn Thr Asn Ile Thr Thr Glu Thr Ser Lys Ile Leu
             100                 105                 110
Leu Gln Lys Asn Met Gln Ile Ala Asn His Thr Leu Lys Tyr Gly Thr
             115                 120                 125
Gln Ala Arg Lys Phe Asp Val Asn Gln Leu Gln Asn Thr Thr Ile Lys
    130                 135                 140
Arg Ile Ile Lys Lys Val Gln Asp Leu Glu Arg Ala Ala Leu Pro Ala
145                 150                 155                 160
Gln Glu Leu Glu Glu Tyr Asn Lys Ile Leu Leu Asp Met Glu Thr Thr
                 165                 170                 175
Tyr Ser Val Ala Thr Val Cys His Pro Asn Gly Ser Cys Leu Gln Leu
             180                 185                 190
Glu Pro Asp Leu Thr Asn Val Met Ala Thr Ser Arg Lys Tyr Glu Asp
             195                 200                 205
Leu Leu Trp Ala Trp Glu Gly Trp Arg Asp Lys Ala Gly Arg Ala Ile
    210                 215                 220
Leu Gln Phe Tyr Pro Lys Tyr Val Glu Leu Ile Asn Gln Ala Ala Arg
225                 230                 235                 240
Leu Asn Gly Tyr Val Asp Ala Gly Asp Ser Trp Arg Ser Met Tyr Glu
                 245                 250                 255
Thr Pro Ser Leu Glu Gln Asp Leu Glu Arg Leu Phe Gln Glu Leu Gln
             260                 265                 270
Pro Leu Tyr Leu Asn Leu His Ala Tyr Val Arg Arg Ala Leu His Arg
         275                 280                 285
His Tyr Gly Ala Gln His Ile Asn Leu Glu Gly Pro Ile Pro Ala His
    290                 295                 300
Leu Leu Gly Asn Met Trp Ala Gln Thr Trp Ser Asn Ile Tyr Asp Leu
305                 310                 315                 320
Val Val Pro Phe Pro Ser Ala Pro Ser Met Asp Thr Thr Glu Ala Met
                 325                 330                 335
```

```
Leu Lys Gln Gly Trp Thr Pro Arg Arg Met Phe Lys Glu Ala Asp Asp
         340                 345                 350
Phe Phe Thr Ser Leu Gly Leu Leu Pro Val Pro Pro Glu Phe Trp Asn
         355                 360                 365
Lys Ser Met Leu Glu Lys Pro Thr Asp Gly Arg Glu Val Val Cys His
370                 375                 380
Ala Ser Ala Trp Asp Phe Tyr Asn Gly Lys Asp Phe Arg Ile Lys Gln
385                 390                 395                 400
Cys Thr Thr Val Asn Leu Glu Asp Leu Val Val Ala His His Glu Met
                 405                 410                 415
Gly His Ile Gln Tyr Phe Met Gln Tyr Lys Asp Leu Pro Val Ala Leu
                 420                 425                 430
Arg Glu Gly Ala Asn Pro Gly Phe His Glu Ala Ile Gly Asp Val Leu
         435                 440                 445
Ala Leu Ser Val Ser Thr Pro Lys His Leu His Ser Leu Asn Leu Leu
450                 455                 460
Ser Ser Glu Gly Gly Ser Asp Glu His Asp Ile Asn Phe Leu Met Lys
465                 470                 475                 480
Met Ala Leu Asp Lys Ile Ala Phe Ile Pro Phe Ser Tyr Leu Val Asp
                 485                 490                 495
Gln Trp Arg Trp Arg Val Phe Asp Gly Ser Ile Thr Lys Glu Asn Tyr
         500                 505                 510
Asn Gln Glu Trp Trp Ser Leu Arg Leu Lys Tyr Gln Gly Leu Cys Pro
         515                 520                 525
Pro Val Pro Arg Thr Gln Gly Asp Phe Asp Pro Gly Ala Lys Phe His
    530                 535                 540
Ile Pro Ser Ser Val Pro Tyr Ile Arg Tyr Phe Val Ser Phe Ile Ile
545                 550                 555                 560
Gln Phe Gln Phe His Glu Ala Leu Cys Gln Ala Ala Gly His Thr Gly
                 565                 570                 575
Pro Leu His Lys Cys Asp Ile Tyr Gln Ser Lys Glu Ala Gly Gln Arg
         580                 585                 590
Leu Ala Thr Ala Met Lys Leu Gly Phe Ser Arg Pro Trp Pro Glu Ala
         595                 600                 605
Met Gln Leu Ile Thr Gly Gln Pro Asn Met Ser Ala Ser Ala Met Leu
    610                 615                 620
Ser Tyr Phe Lys Pro Leu Leu Asp Trp Leu Arg Thr Glu Asn Glu Leu
625                 630                 635                 640
His Gly Glu Lys Leu Gly Trp Pro Gln Tyr Asn Trp Thr Pro Asn Ser
                 645                 650                 655
Ala Arg Ser Glu Gly Pro Leu Pro Asp Ser Gly Arg Val Ser Phe Leu
         660                 665                 670
Gly Leu Asp Leu Asp Ala Gln Gln Ala Arg Val Gly Gln Trp Leu Leu
         675                 680                 685
Leu Phe Leu Gly Ile Ala Leu Leu Val Ala Thr Leu Gly Leu Ser Gln
    690                 695                 700
Arg Leu Phe Ser Ile Arg His Arg Ser Leu His Arg His Ser His Gly
705                 710                 715                 720
Pro Gln Phe Gly Ser Glu Val Glu Leu Arg His Ser
                 725                 730
```

( 2 ) INFORMATION FOR SEQ ID NO:3:

( i ) SEQUENCE CHARACTERISTICS:

( A ) LENGTH: 5 amino acids
        ( B ) TYPE: amino acid
        ( C ) STRANDEDNESS: single
        ( D ) TOPOLOGY: linear ( i i ) MOLECULE TYPE: polypeptide ( x i ) SEQUENCE DESCRIPTION: SEQ ID NO:3:

His   Glu   Met   Gly   His